US009561280B2

(12) United States Patent
Nishihata et al.

(10) Patent No.: US 9,561,280 B2
(45) Date of Patent: Feb. 7, 2017

(54) AQUEOUS LIQUID BROMFENAC COMPOSITION HAVING PRESERVATIVE EFFICACY

(71) Applicant: SENJU PHARMACEUTICAL CO., LTD., Osaka (JP)

(72) Inventors: Shuichi Nishihata, Hyogo (JP); Wakiko Asayama, Hyogo (JP); Suzuka Iemoto, Hyogo (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/793,886

(22) Filed: Jul. 8, 2015

(65) Prior Publication Data

US 2015/0306222 A1 Oct. 29, 2015

Related U.S. Application Data

(62) Division of application No. 13/978,258, filed as application No. PCT/JP2012/050903 on Jan. 18, 2012, now Pat. No. 9,107,888.

(30) Foreign Application Priority Data

Jan. 18, 2011 (JP) ................ 2011-007898
Sep. 13, 2011 (JP) ................ 2011-199480
Dec. 28, 2011 (JP) ................ 2011-289640

(51) Int. Cl.
*A61K 31/196* (2006.01)
*A61K 47/18* (2006.01)
*A61K 31/14* (2006.01)
*A61K 9/08* (2006.01)
*A61K 47/26* (2006.01)
*A61K 9/00* (2006.01)

(52) U.S. Cl.
CPC ........... *A61K 47/186* (2013.01); *A61K 9/08* (2013.01); *A61K 31/14* (2013.01); *A61K 31/196* (2013.01); *A61K 47/18* (2013.01); *A61K 47/26* (2013.01); *A61K 9/0043* (2013.01); *A61K 9/0046* (2013.01); *A61K 9/0048* (2013.01)

(58) Field of Classification Search
CPC ...................... A61K 31/14; A61K 31/195
See application file for complete search history.

(56) References Cited

U.S. PATENT DOCUMENTS

| 4,910,225 | A | 3/1990 | Ogawa et al. |
| 5,414,011 | A | 5/1995 | Fu et al. |
| 5,942,508 | A | 8/1999 | Sawa |
| 6,274,592 | B1 | 8/2001 | Sawa |
| 7,829,544 | B2 | 11/2010 | Sawa |
| 2005/0239895 | A1 | 10/2005 | Sawa et al. |
| 2007/0021507 | A1 | 1/2007 | Sawa |
| 2007/0287749 | A1 | 12/2007 | Sawa et al. |
| 2010/0324031 | A1 | 12/2010 | Kabra |

FOREIGN PATENT DOCUMENTS

| CN | 101313899 | 12/2008 |
| JP | 2-286627 | 11/1990 |
| JP | 2683676 | 8/1997 |
| JP | 10-109930 | 4/1998 |
| JP | 10-279481 | 10/1998 |
| JP | 10-279503 | 10/1998 |
| JP | 2004/064828 | 10/1998 |
| JP | 2954356 | 7/1999 |
| JP | 2005/046700 | 5/2005 |
| JP | 2009-161454 | 7/2009 |
| WO | 96/14829 | 5/1996 |
| WO | 2006/049250 | 5/2006 |

OTHER PUBLICATIONS

International Search Report issued Mar. 19, 2012 in International (PCT) Application No. PCT/JP2012/050903.
International Preliminary Report on Patentability issued Jul. 23, 2013 and English translation of Written Opinion of the International Searching Authority issued Mar. 19, 2012 in corresponding International Application No. PCT/JP2012/050903.
Liu et al. (AAPS PharmSciTech, vol. 10, No. 4, Dec. 2009).
N. Takahashi et al., "Antiseptic Agents and Their Influences on Eyes", Ophthalmology, vol. 31, pp. 43-48, 1989.
J. Shimazaki, "Antiseptic Agents in Ophthalmic Solutions and Adverse Reactions to Them", Ophthalmology, vol. 33, pp. 533-538, 1991.

*Primary Examiner* — Zohreh Fay
(74) *Attorney, Agent, or Firm* — Wenderoth, Lind & Ponack, L.L.P.

(57) ABSTRACT

An aqueous liquid bromfenac composition containing (a) bromfenac or a salt thereof and (b) benzalkonium chloride, characterized by that the composition has preservative efficacy and that the concentration of (b) benzalkonium chloride is higher than 0.0005% and lower than 0.005%.

3 Claims, No Drawings

# AQUEOUS LIQUID BROMFENAC COMPOSITION HAVING PRESERVATIVE EFFICACY

This application is a divisional of application Ser. No. 13/978,258, which is the National Stage of International Application No. PCT/JP2012/050903, filed Jan. 18, 2012.

TECHNICAL FIELD

The present invention relates to an aqueous liquid bromfenac composition in which a base containing a low concentration of benzalkonium chloride is used and which has preservative efficacy and stability. The present invention also relates to a method for preparing an aqueous liquid bromfenac composition having preservative efficacy by combining bromfenac and an aqueous base composition which contains benzalkonium chloride but does not have sufficient preservative efficacy. The present invention also relates to a method for enhancing the preservative efficacy of an aqueous solution.

BACKGROUND ART

Generally, a preservative is indispensable in (multidose) aqueous liquid compositions. A representative of such a preservative is Benzalkonium chloride. However, frequent application of an ophthalmic solution containing benzalkonium chloride or application thereof to those who have corneal injury or abnormal tear dynamics such as dry eye syndrome causes side effects and corneal damage (Non Patent Literature 1 and 2). Therefore, it is desirable that the concentration of benzalkonium chloride added to ophthalmic solutions etc. is low. Considering both preservative efficacy and safety, a desirable concentration of benzalkonium chloride added to an ophthalmic solution is said to be 0.002% to 0.005% (Non Patent Literature 1). Aqueous liquid bromfenac compositions containing 0.001% or 0.005% benzalkonium chloride are known (Patent Literature 1 to 7). However, the preservative efficacy of the compositions is unknown.

Bromfenac (2-amino-3-(4-bromobenzoyl)phenylacetic acid) is a non-steroidal anti-inflammatory drug of which the preservative efficacy is unknown.

Benzalkonium chloride is a cationic surfactant which is widely used as a preservative for topical aqueous liquids as mentioned above. A preferred concentration of benzalkonium chloride, in particular in ophthalmic solutions, is 0.002% to 0.005%, but the preservative efficacy of benzalkonium chloride can decline under the influence of other substances in an aqueous base. For example, a large amount of a non-ionic surfactant added to an aqueous liquid impairs the preservative efficacy of benzalkonium chloride (Patent Literature 8). It is also known that benzalkonium chloride forms complexes with other substances in an aqueous liquid, resulting in impaired preservative efficacy. In particular, it is reported that a combination of a non-steroidal anti-inflammatory drug (NSAID) and a quaternary ammonium salt such as benzalkonium chloride forms a complex, resulting in decline in the preservative efficacy (Patent Literature 9 and 10).

No aqueous liquid bromfenac composition which has sufficient preservative efficacy and stability as a result of combining bromfenac and a base which contains benzalkonium chloride but does not have sufficient preservative efficacy has so far been reported.

CITATION LIST

Patent Literature

[PTL 1] JP 10-279481 A (U.S. Pat. No. 5,942,508)
[PTL 2] JP 10-279503 A (U.S. Pat. No. 6,274,592)
[PTL 3] JP 2004-064828 W (US 2005-239895 A)
[PTL 4] JP 2005-046700 W (U.S. Pat. No. 7,829,544)
[PTL 5] JP 2006-049250 W (US 2007-021507 A)
[PTL 6] JP Pat. No. 2683676 (U.S. Pat. No. 4,910,225)
[PTL 7] CN 101313899 A
[PTL 8] JP 10-109930 A
[PTL 9] JP 02-286627 A (U.S. Pat. No. 5,414,011)
[PTL 10] JP Pat. No. 2954356 (WO 96/14829)

Non Patent Literature

[NPL 1] *Ophthalmology* Vol. 31 43-48, 1989 (published by Kanehara & Co., Ltd.)
[NPL 2] *Ophthalmology* Vol. 33 533-538, 1991 (published by Kanehara & Co., Ltd.)

SUMMARY OF INVENTION

Technical Problem

In view of the above problems, an object of the present invention is to provide an aqueous liquid bromfenac composition having preservative efficacy and stability by combining bromfenac and an aqueous base which contains benzalkonium chloride but does not have sufficient preservative efficacy. Another object of the present invention is to provide a method for preparing an aqueous liquid bromfenac composition having preservative efficacy by combining bromfenac and an aqueous base which contains benzalkonium chloride but does not have sufficient preservative efficacy. Still another object of the present invention is to provide a method for enhancing the preservative efficacy of an aqueous solution for use in ophthalmic solutions, etc.

Solution to Problem

In view of the above problems, the present inventors made extensive research, and found that an aqueous liquid bromfenac composition having preservative efficacy can be prepared by combining bromfenac sodium and an aqueous base composition which contains up to 0.005% benzalkonium chloride but does not have sufficient preservative efficacy, as the base of the aqueous liquid composition containing bromfenac sodium. The present inventors also found a method for preparing an aqueous liquid bromfenac composition having preservative efficacy by combining bromfenac sodium and the above-mentioned aqueous base composition which contains benzalkonium chloride but does not have sufficient preservative efficacy.

As described above, it is known that a combination of a non-steroidal anti-inflammatory drug (NSAID) and a quaternary ammonium salt forms a complex, resulting in decline in the preservative efficacy. Since bromfenac is a non-steroidal anti-inflammatory drug and benzalkonium chloride is a quaternary ammonium salt, it is expected that combining these two results in decline in the preservative efficacy. However, unexpectedly, a combination of bromfenac and benzalkonium chloride both of which were at a concentration insufficient for exerting preservative efficacy by itself significantly enhanced the preservative efficacy specifically against *Pseudomonas aeruginosa*, that is, provided improved preservative efficacy to the aqueous liquid composition. The obtained aqueous liquid bromfenac composition had also excellent stability.

The present inventors also found that an aqueous liquid bromfenac composition having preservative efficacy can be prepared by combining (a) bromfenac or a salt thereof and (b) benzalkonium chloride, even when the added amount of benzalkonium chloride is reduced to the minimum. In this way, the side effect of the aqueous liquid bromfenac composition containing benzalkonium chloride can be reduced.

The present inventors also found that bacterial proliferation in an aqueous solution can be suppressed by adding bromfenac or a salt thereof to the solution. Thus, the addition of bromfenac or a salt thereof to an aqueous solution can enhance the preservative efficacy of the solution, and therefore, a small amount of a preservative is sufficient to suppress the proliferation of bacteria or the like in the aqueous solution and hence a highly safe aqueous liquid composition etc. can be obtained.

Based on the above findings, the inventors conducted further research and completed the present invention.

That is, the present invention relates to the following (1) to (17).

(1) An aqueous liquid bromfenac composition containing (a) bromfenac or a salt thereof and (b) benzalkonium chloride, characterized by that the composition has preservative efficacy and that the concentration of (b) benzalkonium chloride is higher than 0.0005% and lower than 0.005%.
(2) The aqueous liquid composition of the above (1), wherein the concentration of (a) bromfenac or a salt thereof is 0.01% to 10%.
(3) The aqueous liquid composition of the above (1) or (2), wherein the concentration of (b) benzalkonium chloride is 0.00075% to 0.003%.
(4) The aqueous liquid composition of any one of the above (1) to (3), further containing (c) at least one kind selected from the group consisting of a non-ionic surfactant and a water-soluble polymer.
(5) The aqueous liquid composition of the above (4), wherein the total concentration of (c) at least one kind selected from the group consisting of a non-ionic surfactant and a water-soluble polymer is 0.0001% to 5%.
(6) The aqueous liquid composition of the above (4) or (5), wherein the at least one kind selected from the group consisting of a non-ionic surfactant and a water-soluble polymer is a non-ionic surfactant.
(7) The aqueous liquid composition of any one of the above (4) to (6), wherein the non-ionic surfactant is polysorbate 80.
(8) The aqueous liquid composition of any one of the above (4) to (7), wherein the concentration of the non-ionic surfactant is 0.025% or higher and lower than 0.25%.
(9) The aqueous liquid composition of any one of the above (4) to (8), wherein the concentration of the non-ionic surfactant is 0.025% to 0.15%.
(10) The aqueous liquid composition of any one of the above (4) to (8), wherein the concentration of the non-ionic surfactant is 0.05% or higher and lower than 0.25%.
(11) The aqueous liquid composition of the above (4) or (5), wherein the at least one kind selected from the group consisting of a non-ionic surfactant and a water-soluble polymer is a water-soluble polymer.
(12) The aqueous liquid composition of any one of the above (4), (5), and (11), wherein the water-soluble polymer is at least one kind selected from the group consisting of hydroxyethyl cellulose and povidone.
(13) The aqueous liquid composition of any one of the above (4), (5), (11), and (12), wherein the concentration of the water-soluble polymer is 0.01% to 1.4%.
(14) The aqueous liquid composition of any one of the above (1) to (13), which is an ophthalmic solution, a nasal solution, or an otic solution.
(15) A method for providing preservative efficacy to an aqueous liquid composition containing bromfenac or a salt thereof, the method comprising combining bromfenac or a salt thereof and an aqueous base which contains benzalkonium chloride but does not have sufficient preservative efficacy.
(16) A method for enhancing the preservative efficacy of an aqueous solution, the method comprising adding bromfenac or a salt thereof to the solution.
(17) The method of the above (16), wherein the enhancement of the preservative efficacy is evidenced by reduction in viable cell count of Staphylococcus aureus (S. aureus).

The present invention also relates to the following (A1) to (A10).

(A1) An aqueous liquid bromfenac composition containing (a) bromfenac or a salt thereof and (b) benzalkonium chloride, characterized by that the concentration of (b) benzalkonium chloride is higher than 0.0005% and lower than 0.005%.
(A2) The aqueous liquid composition of the above (A1), wherein the concentration of (b) benzalkonium chloride is higher than 0.0005% and lower than 0.002%.
(A3) The aqueous liquid composition of the above (A1) or (A2), which has preservative efficacy.
(A4) The aqueous liquid composition of any one of the above (A1) to (A3), wherein the concentration of (a) bromfenac or a salt thereof is 0.01% to 10%.
(A5) The aqueous liquid composition of any one of the above (A1) to (A4), wherein the concentration of (b) benzalkonium chloride is 0.00075% to 0.0015%.
(A6) The aqueous liquid composition of any one of the above (A1) to (A5), further containing (c) at least one kind selected from the group consisting of a non-ionic surfactant and a water-soluble polymer.
(A7) The aqueous liquid composition of the above (A6), wherein the non-ionic surfactant is polysorbate 80.
(A8) The aqueous liquid composition of the above (A6) or (A7), wherein the concentration of the non-ionic surfactant is 0.001% to 5%.
(A9) The aqueous liquid composition of any one of the above (A1) to (A8), which is an ophthalmic solution, a nasal solution, or an otic solution.
(A10) A method for providing preservative efficacy to an aqueous liquid composition containing bromfenac or a salt thereof, the method comprising combining bromfenac or a salt thereof and an aqueous base which contains benzalkonium chloride but does not have sufficient preservative efficacy.

Advantageous Effects of Invention

According to the present invention, an aqueous liquid bromfenac composition having preservative efficacy and stability can be obtained even when the added amount of benzalkonium chloride is reduced to the minimum. According to the present invention, an aqueous liquid bromfenac composition having preservative efficacy can be provided by combining bromfenac and an aqueous base which contains a low concentration of benzalkonium chloride or contains benzalkonium chloride but does not have sufficient preservative efficacy. The aqueous liquid bromfenac composition has the preservative efficacy which complies with <51> ANTIMICROBIAL EFFECTIVENESS TESTING (preservatives-effectiveness tests) of "Microbiological tests" specified in the United States Pharmacopeia (USP) 32. Therefore, the present invention can provide a bromfenac aqueous liquid composition which causes fewer side effects and is safe and stable.

In addition, according to the present invention, the preservative efficacy of an aqueous solution can be enhanced by adding bromfenac or a salt thereof to the solution. Therefore, according to the present invention, a small amount of a preservative is sufficient to suppress the proliferation of bacteria or the like in the aqueous solution and thus a highly safe aqueous liquid composition can be provided.

DESCRIPTION OF EMBODIMENTS

Definitions

As used herein, "Preservatives-Effectiveness Tests" refers to the method specified in the Japanese Pharmacopoeia Fifteenth Edition unless otherwise stated.

In the method, with the use of bacteria, such as *Staphylococcus aureus, Escherichia coli,* and *Pseudomonas aeruginosa*, and fungi, such as *Candida albicans* and *Aspergillus brasiliensis (niger)*, as test microorganisms, the following procedures (i) to (iv) are performed.

(i) Each of the above-mentioned five strains for testing is inoculated onto the surface of a slant agar medium and precultured. As the agar medium for preculture, a soybean casein digest agar medium is used for the bacteria, and a Sabouraud glucose agar medium is used for the fungi. The bacteria are precultured at 30 to 35° C. for 18 to 24 hours, *Candida albicans* is precultured at 20 to 25° C. for 40 to 48 hours, and *Aspergillus brasiliensis (niger)* is precultured at 20 to 25° C. for a week or until sufficient sporulation is achieved.

(ii) The aqueous liquid composition to be tested as a sample is dispensed to 5 sterile stoppered test tubes so that each tube contains 10 mL of the sample. To these, test microorganisms of (i) are inoculated at $10^5$ to $10^6$ cells/mL, and the thus prepared mixed samples are stored at 20 to 25° C. in light-shielded conditions. The test microorganism are not mixed with each other but separately inoculated into the samples.

(iii) From each of the mixed samples, 1 mL is sampled after 1 week, 2 weeks, and 4 weeks of storage, and diluted with 9 mL of physiological saline. The same dilution is further performed twice or 3 times, and 1 mL of each diluent is transferred into separate sterile petri dishes.

(iv) Subsequently, a soybean casein digest agar medium supplemented with 0.1% lecithin and 0.7% polysorbate 80 is poured into the petri dishes containing the bacteria, and a Sabouraud glucose agar medium supplemented with 0.1% lecithin and 0.7% polysorbate 80 is poured into the petri dishes containing the fungi. After culturing under the conditions shown below, the number of the formed colonies is counted, and the theoretical cell count in 1 mL of each mixed sample is calculated.

Culture conditions for bacteria: at 30 to 35° C. for about 3 to 5 days

Culture conditions for fungi: at 20 to 25° C. for about 5 days

After the above (i) to (iv) are completed, the sample is judged as "having preservative efficacy" in cases where the sample satisfies all the following criteria: all the bacterial viable cell counts (*Staphylococcus aureus, Escherichia coli,* and *Pseudomonas aeruginosa*) in the mixed solutions after 14 days of storage are all reduced to 0.1% of the inoculated cell counts or less, and the bacterial viable cell counts after 28 days of storage are still at the same level as those after 14 days of storage or less; and all the fungal viable cell counts in the mixed solutions after 14 days of storage and after 28 days of storage are all at the same level as the inoculated cell counts or less. In the cases where any one of the above bacteria and fungi does not satisfy the above criteria, the sample is judged as "not having sufficient preservative efficacy".

In the <51> ANTIMICROBIAL EFFECTIVENESS TESTING (preservatives-effectiveness tests) of "Microbiological tests" specified in the United States Pharmacopeia (USP) 32, after the above (i) to (iv) are completed, the sample is judged as "having preservative efficacy" in cases where the sample satisfies all the following criteria: (1) all the bacterial viable cell counts (*Staphylococcus aureus, Escherichia coli,* and *Pseudomonas aeruginosa*) in the mixed solutions after 7 days of storage are reduced to 10% of the inoculated cell counts or less, all the viable cell counts after 14 days of storage are reduced to 0.1% of the inoculated cell counts or less, and all the viable cell counts after 28 days of storage remain the same level as those after 14 days of storage or less, and (2) all the fungal viable cell counts in the mixed solutions after 7, 14, and 28 days of storage are at the same level as the inoculated cell counts or less. In the cases where any one of the above bacteria and fungi does not satisfy the above criteria, the sample is judged as "not having sufficient preservative efficacy".

The term "stable" or "having stability" means that the preservative efficacy is retained for, for example, at least 1 year of storage and no changes are observed in the properties.

As used herein, an aqueous liquid composition "having preservative efficacy" is the one that is judged as "having preservative efficacy" in the above-mentioned preservatives-effectiveness tests specified in the Japanese Pharmacopoeia or the United States Pharmacopeia (USP). An aqueous liquid composition "not having sufficient preservative efficacy" is the one that is judged as "not having sufficient preservative efficacy" in the above-mentioned preservatives-effectiveness tests. The term "preservative efficacy" is synonymous with "antiseptic efficacy", and the term "preservative" is synonymous with "antiseptic".

As used herein, an "aqueous base" refers to an aqueous solution prepared by adding 1 or more additives to water as a vehicle, and "an aqueous liquid" refers to a liquid prepared by adding 1 or more pharmacologically active ingredient to the aqueous base, unless otherwise stated.

As used herein, a "low concentration" refers to a concentration higher than 0.0005% and lower than 0.005%, unless otherwise stated.

As used herein, % means w/v % (g/100 mL), unless otherwise stated.

Herein, as described above, a benzalkonium chloride-containing aqueous base whose efficacy as a preservative has declined under the influence of another substance and has been judged as "not having sufficient preservative efficacy" in the above-mentioned preservatives-effectiveness tests specified in the Japanese Pharmacopoeia or the United States Pharmacopeia (USP) is described as an "aqueous base which contains benzalkonium chloride but does not have sufficient preservative efficacy".

As used herein, a "method for providing preservative efficacy" means a method comprising combining a composition and/or a base both of which were at a concentration insufficient for exerting preservative efficacy by itself to give a composition having preservative efficacy.

The present invention provides an aqueous liquid bromfenac composition containing bromfenac and a low concentration of benzalkonium chloride. The aqueous liquid bromfenac composition of the present invention has preservative efficacy.

The aqueous liquid bromfenac composition of the present invention having preservative efficacy is an aqueous liquid composition containing (a) bromfenac or a salt thereof and (b) benzalkonium chloride, and the concentration of (b) benzalkonium chloride is higher than 0.0005% and lower than 0.005%.

The salt of bromfenac added to the aqueous liquid composition of the present invention is not particularly limited as long as the salt is pharmaceutically acceptable. Examples of the salt include, alkali metal salts, such as sodium salt and potassium salt; alkaline earth metal salts, such as calcium salt and magnesium salt, and these can be used as appropriate unless the objects of the present invention are hindered. Depending on the conditions of synthesis, recrystallization, etc., the above compounds may be obtained in the form of a hydrate, which can be used in the present invention without any inconvenience. Among the salts of bromfenac, preferred is sodium salt.

The concentration of bromfenac or a salt thereof in the aqueous liquid composition of the present invention is usually about 0.001% to 10%, preferably about 0.01% to 10%, more preferably about 0.01% to 1%, still more preferably about 0.02% to 0.15%, and particularly preferably about 0.02% to 0.1%.

In another preferred embodiment of the present invention, the concentration of bromfenac or a salt thereof is preferably about 0.05% to 0.15%.

Bromfenac and a pharmacologically acceptable salt thereof can be appropriately produced by the method according to JP 52-23052 A (corresponding to U.S. Pat. No. 4,045,576) or an equivalent method (for example, FDA Drug Master File #16414, or the like). Depending on the conditions of synthesis, recrystallization, etc., bromfenac and a pharmacologically acceptable salt thereof are usually obtained as hydrates thereof. Examples of the hydrate include 1/2 hydrate, monohydrate, and 3/2 hydrate, and preferred is 3/2 hydrate.

As used herein, the term benzalkonium chloride has the same meaning as a chloride of benzalkonium.

The generally used benzalkonium chloride, which is represented by the rational formula: $[C_6H_5CH_2N(CH_3)_2R]Cl$, is a mixture of compounds having $C_8H_{17}$ to $C_{18}H_{37}$ as the alkyl group R in the rational formula as described in the pharmacopoeias of Japan, the U.S., and Europe. Shown below are the descriptions of benzalkonium chloride in the pharmacopoeias of Japan, the U.S., and Europe.

Japanese Pharmacopoeia: represented by the formula $[C_6H_5CH_2N(CH_3)_2R]Cl$, in which R is $C_8H_{17}$ to $C_{18}H_{37}$, mainly comprising $C_{12}H_{25}$ and $C_{14}H_{29}$.

The U.S. Pharmacopeia (USP): a mixture of alkylbenzyldimethylammonium chlorides represented by the formula $[C_4H_5CH_2N(CH_3)_2R]Cl$, in which R is a mixture of all or some of alkyl groups equal to or longer than $C_8H_{17}$, mainly comprising $C_{12}H_{25}$, $C_{14}H_{29}$, and $C_{18}H_{38}$.

European Pharmacopoeia: a mixture of alkylbenzyldimethylammonium chlorides with alkyl chain lengths of $C_8$ to $C_{18}$.

As used herein, "benzalkonium chloride" usually refers to the mixture of benzalkonium chlorides as described above.

When benzalkonium chloride is designated by the number of carbon atoms, the number denotes the length of the carbon chain of the alkyl group represented by "R" in the above-mentioned pharmacopoeias.

The benzalkonium chloride added to the aqueous liquid composition of the present invention may be one of those represented by the rational formula: $[C_6H_5CH_2N(CH_3)_2R]Cl$ in which the alkyl group R is $C_8H_{17}$ to $C_{18}H_{37}$, or a mixture thereof. Preferred is a mixture represented by the rational formula in which R mainly comprising $C_{12}H_{25}$ and $C_{14}H_{29}$, and more preferred is a mixture represented by the rational formula in which R is a mixture in which the amount of $C_{12}H_{25}$ is about 80 to 85% and the amount of $C_{12}H_{25}$ and $C_{14}H_{29}$ together is about 98% or more.

The lower limit of the concentration of benzalkonium chloride in the aqueous liquid composition of the present invention is usually higher than about 0.0005%, preferably about 0.0006%, more preferably about 0.0007%, still more preferably about 0.00075%, particularly preferably about 0.0008%, and most preferably about 0.001%. The upper limit thereof is usually lower than about 0.005%, preferably about 0.004%, more preferably about 0.003%, still more preferably about 0.002%, particularly preferably about 0.0015%, and most preferably about 0.001%. Even when the concentration of benzalkonium chloride is within the above range, such benzalkonium chloride can be combined with bromfenac or a salt thereof to give an aqueous liquid composition having preservative efficacy.

The concentration range of benzalkonium chloride blended in the aqueous liquid composition of the present invention is usually higher than about 0.0005% and lower than about 0.005%, preferably about 0.00075% to 0.003%, and still more preferably about 0.001% to 0.002%.

The aqueous liquid composition of the present invention has preservative efficacy because the composition contains (a) bromfenac or a salt thereof and (b) benzalkonium chloride, the concentration of (b) being higher than 0.0005%. Therefore, the composition need not contain any preservatives other than benzalkonium chloride. The composition may, however, further contain an additional preservative if desired.

As the additional preservative, one or more kinds of, for example, chlorhexidine salt, benzethonium chloride, p-hydroxybenzonates, benzyl alcohol, p-chlorometaxylenol, chlorocresol, phenethyl alcohol, sorbic acid or a salt thereof, thimerosal, chlorobutanol, boric acid, sodium edetate, and the like. The amount of the additional preservative is not particularly limited as long as the effect of the present invention is exerted, and can be determined as appropriate.

The aqueous liquid composition of the present invention can further contain a compound having a surface-activating action. Examples of the compound having a surface-activating action include a non-ionic surfactant, a water-soluble polymer, and the like. Such an aqueous liquid composition further containing at least one kind selected from the group consisting of a non-ionic surfactant and a water-soluble polymer is a preferred embodiment of the present invention. Inter alia, more preferred is the one containing a non-ionic surfactant.

The total concentration of the non-ionic surfactant and the water-soluble polymer in the aqueous liquid composition of the present invention is usually about 0.0001% to 5%, preferably about 0.01% to 3%, more preferably about 0.01% to 1.4%, still more preferably about 0.025% to lower than 0.25%, particularly preferably about 0.025% to 0.15%, and most preferably about 0.05% to 0.15%.

In another preferred embodiment of the present invention, the total concentration of the non-ionic surfactant and the water-soluble polymer is further preferably about 0.05% to 0.3%.

Examples of the non-ionic surfactant in the aqueous liquid composition of the present invention include polyoxyethylene sorbitan fatty acid esters, polyoxyethylene hydrogenated castor oils, alkyl aryl polyether alcohol-type polymers, polyoxyethylene fatty acid esters, polyoxyethylene polyoxypropylene glycols, and sucrose fatty acid esters. Preferred are polyoxyethylene sorbitan fatty acid esters, such as polyoxyethylene sorbitan monooleate, polyoxyethylene sorbitan monolaurate, polyoxyethylene sorbitan monopalmitate, polyoxyethylene sorbitan monostearate, and polyoxyethylene sorbitan tristearate; polyoxyethylene hydrogenated castor oils, such as polyoxyethylene hydrogenated castor oil 10, polyoxyethylene hydrogenated castor oil 40, polyoxyethylene hydrogenated castor oil 50, and polyoxyethylene hydrogenated castor oil 60; alkyl aryl polyether alcohol-type polymers, such as tyloxapol; and polyoxyethylene fatty acid esters, such as polyoxyl stearate. Inter alia, further preferred are polysorbate 80, polyoxyethylene hydrogenated castor oil 60, tyloxapol, polyoxyl 40 stearate, etc., and particularly preferred is polysorbate 50. These non-ionic surfactants may be used alone or as a mixture of two or more thereof. The lower limit of the concentration of the non-ionic surfactant in the aqueous liquid composition is usually about 0.001%, preferably about 0.005%, more preferably about 0.01%, still more preferably about 0.05%, and particularly preferably about 0.1%. The upper limit of the concentration of the non-ionic surfactant is usually about 5%, preferably about 2%, more preferably about 1%, still more preferably about 0.5%, further more preferably about 0.4%, particularly preferably about 0.3%, particularly preferably about lower than 0.25%, particularly preferably about 0.2%, and most preferably about 0.15% or lower.

The concentration of the non-ionic surfactant in the aqueous liquid composition of the present invention is preferably about 0.001% to 5%, more preferably about 0.01% to 1%, still more preferably about 0.01% to lower than 0.25%, further preferably about 0.025% to lower than 0.25%, particularly preferably about 0.025% to 0.15%, and most preferably about 0.1% to 0.15%.

In another preferred embodiment of the present invention, the concentration of the non-ionic surfactant is preferably about 0.05% to lower than 0.25%, and particularly preferably about 0.1% to 0.2%.

Examples of the water-soluble polymer in the aqueous liquid composition of the present invention include vinyl polymers, such as povidone (polyvinyl pyrrolidone) and polyvinyl alcohol; cellulose polymers, such as hydroxyethylcellulose, hydroxypropylcellulose, methylcellulose, hydroxypropylmethylcellulose, carboxymethylcellulose; and salts thereof. Preferred are polyvinyl alcohol, hydroxypropylmethylcellulose, salts thereof, etc. These water-soluble polymers may be used alone or as a mixture of two or more thereof. For example, in the cases of vinyl polymers, the lower limit is usually about 0.0001%, preferably about 0.0005%, more preferably about 0.001%, still more preferably about 0.005%, still more preferably about 0.01%, further more preferably about 0.05%, still further more preferably about 0.1%, particularly preferably about 0.5%, and most preferably about 1%. In the cases of vinyl polymers, the upper limit is usually about 5%, preferably about 3%, more preferably about 2%, still more preferably about 1.5%, particularly preferably lower than about 1.5%, and most preferably about 1.4%. For example, in the cases of cellulose polymers, the lower limit is usually about 0.0001%, preferably about 0.0005%, more preferably about 0.001%, still more preferably about 0.005%, further more preferably about 0.01%, particularly preferably about 0.05%, and most preferably about 0.1%. In the cases of cellulose polymers, the upper limit is usually about 5%, preferably about 3%, more preferably about 2%, still more preferably about 1%, further more preferably about lower than about 0.5%, further more preferably about 0.3%, and particularly preferably about 0.2%.

The concentration of the water-soluble polymer in the aqueous liquid composition of the present invention is usually about 0.0001% to 5%, preferably about 0.01% to 3%, more preferably about 0.05% to lower than 1.5%, still more preferably about 0.05% to 1.4%, and most preferably about 0.05% to 0.3%. In another preferred embodiment, the concentration of the water-soluble polymer is preferably about 0.01% to 1.4%. In particular, in the cases of vinyl polymers, the concentration is usually about 0.0001% to 5%, preferably about 0.01% to 3%, more preferably about 0.1% to lower than 1.5%, and most preferably about 1% to 1.4%. In the cases of cellulose polymers, the concentration is usually about 0.0001% to 5%, preferably about 0.01% to 3%, more preferably about 0.05% to lower than 0.5%, and most preferably about 0.05% to 0.3%.

The aqueous liquid composition of the present invention may contain one or more kinds of other active ingredients and/or additives appropriately selected depending on the use or the form of the composition as long as the active ingredients and/or additives do not affect the effect of the present invention. These active ingredients and/or additives may be used alone or as a mixture of two or more thereof. The blending ratio of the additional active ingredient or additive can be determined as appropriate.

Examples of the other active ingredients include an antiviral, an antimicrobial, an antifungal, an antiallergic, an antiphlogistic, a non-steroid antiphlogistic, an antibiotic, a sulfa, a synthetic penicillin, a therapeutic agent for glaucoma, a therapeutic agent for cataract, a miotic, a mydriatic, a topical astringent, a vasoconstrictor, an inhibitor for intraocular pressure increase, a therapeutic agent for ocular hypertension, a surface anesthetic, an α1-blocker, a β-blocker, a β1-blocker, a carbonate dehydratase inhibitor, a selective H1-blocker for topical use, an adrenocorticotropic hormone, vitamin B12, coenzyme type vitamin B2, an anticholinesterase drug, an organic iodine preparation, etc.

Examples of the additives include a carrier generally used for semi-solid preparations or liquid preparations (water, an aqueous solvent, an aqueous or oily base), a thickener, a saccharide, a surfactant, a preservative, a bactericide or antimicrobial, a pH adjuster, a tonicity agent, a flavor or cooling agent, a chelator, and a buffering agent.

The pH of the aqueous liquid composition of the present invention is not particularly limited as long as the pH is acceptable to a living body and the effect of the preservative is not hindered, and is usually about 3.5 to 9, and preferably about 7 to 8.5.

The method for preparing the aqueous liquid composition of the present invention is not particularly limited, and the composition can be prepared by dissolving predetermined amounts of (a) bromfenac or a salt thereof, (b) benzalkonium chloride, and if needed (c) at least one kind selected from the group consisting of a non-ionic surfactant and a water-soluble polymer in water or a buffering solution. After the components are dissolved in water, the pH of the solution is preferably adjusted with hydrochloric acid, sodium hydroxide, or the like so as to be within the above range. The order and method of mixing are not particularly limited, and each component may be dissolved in water or a buffering solution by a known preparation method. The water for the preparation of the aqueous liquid composition is not particularly limited as long as the water is medicinally, pharmaceutically, or physiologically acceptable. Examples of the water include distilled water, purified water, water for injection, and distilled water for injection. The buffering solution is not particularly limited, and examples thereof include a phosphate buffer solution and a citrate buffer solution.

The aqueous liquid composition of the present invention contains (b) benzalkonium chloride at a low concentration of higher than 0.0005% and lower than 0.005%. Although (b) benzalkonium chloride is at a concentration insufficient to exert preservative efficacy by itself, the aqueous liquid composition has preservative efficacy because of the presence of (a) bromfenac or a salt thereof. The aqueous liquid bromfenac composition of the present invention is particularly effective in reducing *Pseudomonas aeruginosa*. The presence or absence of the preservative efficacy of the aqueous liquid bromfenac composition of the present invention can be confirmed by the preservatives-effectiveness tests described above.

The aqueous liquid composition of the present invention may be any of a suspension, an emulsion, a gel, and an aqueous solution, but preferably an aqueous solution.

The aqueous liquid composition of the present invention can be used as an internal solution, an injection, an external solution, an ophthalmic solution, an otological solution, etc. As the otological solution, a nasal solution is preferred. Inter alia, the aqueous liquid composition of the present invention is preferably an ophthalmic solution, a nasal solution, or an otic solution. More preferred is an ophthalmic solution. The aqueous liquid composition of the present invention may be filled into a unit dose container, a container with a filter, a multidose container. Since the composition has preservative efficacy, the composition is suitable for filling into a multidose container.

The aqueous liquid composition of the present invention is preferably used for mammals, such as a human, a rat, a mouse, a rabbit, a cow, a pig, a dog, and a cat.

The aqueous liquid composition of the present invention is used as, for example, an ophthalmic solution to be topically administered for treating an inflammatory disease. The composition is suitably used for the treatment of, for example, postoperative inflammation, scleritis, blepharitis, hordeolum, conjunctivitis, keratitis, dacryocystitis, dry eye, etc. In addition, the composition can be used for the treatment of retinopathies, such as exudative AMD (age-related macular degeneration), diabetic retinopathy, diabetic macular edema, central retinal vein occlusion, and branch retinal vein occlusion. The aqueous liquid composition is usually administered in an amount of about 1 to 2 drops at a time, about 1 to 6 times daily. The frequency of administration is suitably adjusted depending on the severity of the symptoms being treated, or the like.

In the cases where the aqueous liquid composition of the present invention is used as a nasal solution, the composition is suitably used for the treatment of, for example, acute rhinitis, acute sinusitis, sinusitis (empyema), etc. In the cases where the aqueous liquid composition of the present invention is used as a nasal solution, the composition is usually administered in an amount of about 1 to 2 drops at a time, about 1 to 6 times daily.

The aqueous liquid composition of the present invention is suitably used as an otic solution for the treatment of, for example, cholesteatoma of the external ear canal, acute otitis externa, external ear perichondritis, external ear canal cellulitis, auricular cellulitis, malignant otitis externa, necrotic otitis externa, *Pseudomonas aeruginosa* otitis externa, diffuse external otitis, other infectious otitis externa, or acute otitis media. In the cases where the aqueous liquid composition of the present invention is used as an otic solution, the composition is usually administered in an amount of about 1 to 2 drops at a time, about 1 to 6 times daily.

The present invention includes a method for providing preservative efficacy to an aqueous liquid composition containing bromfenac or a salt thereof, the method comprising combining bromfenac or a salt thereof and an aqueous base which contains benzalkonium chloride but does not have sufficient preservative efficacy.

The aqueous base composition which contains benzalkonium chloride but does not have sufficient preservative efficacy is, for example, an aqueous base which usually contains benzalkonium chloride at a concentration higher than 0.0005% and lower than 0.01% and a compound, such as a non-ionic surfactant, which has an action of impairing the preservative efficacy of benzalkonium chloride. In the present invention, such an aqueous base which contains benzalkonium chloride but does not have sufficient preservative efficacy is combined with bromfenac or a salt thereof, thereby providing preservative efficacy to the thus obtained aqueous liquid composition containing bromfenac or a salt thereof. The aqueous liquid composition obtainable by the present invention contains bromfenac or a salt thereof and benzalkonium chloride, and has preservative efficacy.

In combining bromfenac or a salt thereof and an aqueous base which contains benzalkonium chloride but does not have sufficient preservative efficacy, the order and method of mixing are not particularly limited, and each component may be dissolved in water or a buffering solution by a known preparation method. For example, after an aqueous base which contains benzalkonium chloride but does not have sufficient preservative efficacy is prepared, bromfenac or a salt thereof may be added thereto. Alternatively, to an aqueous liquid composition containing bromfenac or a salt thereof, a predetermined amount of benzalkonium chloride may be added. Alternatively, predetermined amounts of bromfenac or a salt thereof and benzalkonium chloride may be dissolved in the water or the buffering solution described above. The aqueous base which contains benzalkonium chloride but does not have sufficient preservative efficacy preferably contains the above-described compound having a surface-activating action, for example, a non-ionic surfactant and/or a water-soluble polymer. The non-ionic surfactant, the water-soluble polymer, and preferred concentrations thereof in the aqueous base are the same as those of the above-described aqueous liquid composition.

The salts of bromfenac used in the method of the present invention are the same as those used in the above described aqueous liquid bromfenac composition, and are not particularly limited as long as the salts are pharmaceutically acceptable. Examples of the salt include, alkali metal salts, such as sodium salt and potassium salt; alkaline earth metal salts, such as calcium salt and magnesium salt, and these can be used as appropriate unless the objects of the present invention is hindered. Depending on the conditions of synthesis, recrystallization, etc., the above compounds may be obtained in the form of a hydrate, which can be used in the present invention without any inconvenience. Among the salts of bromfenac, preferred is sodium salt.

In the method of the present invention, bromfenac or a salt thereof is added so as to be, in concentration relative to the aqueous liquid composition as the final product, usually about 0.001% to 10%, preferably about 0.01% to 10%, more preferably about 0.01% to 1%, still more preferably about 0.02% to 0.15%, and most preferably about 0.02% to 0.1%.

In another preferred embodiment, bromfenac or a salt thereof is added so as to be, in concentration relative to the aqueous liquid composition as the final product, usually about 0.001% to 10%, preferably about 0.01% to 1%, and more preferably about 0.05% to 0.15%.

Bromfenac and a pharmacologically acceptable salt thereof can be produced as appropriate by the method described above. Depending on the conditions of synthesis, recrystallization, etc., bromfenac and a pharmacologically acceptable salt thereof are usually obtained as hydrates thereof. Examples of the hydrate include 1/2 hydrate, monohydrate, and 3/2 hydrate, and preferred is 3/2 hydrate.

The benzalkonium chloride in the method of the present invention and the preferred embodiment thereof are the same as those described for the above-described aqueous liquid composition.

As described above, the generally used benzalkonium chloride, which is represented by the rational formula: $[C_6H_5CH_2N(CH_3)_2R]Cl$, is usually a mixture of compounds having $C_8H_{17}$ to $C_{18}H_{37}$ as the alkyl group R in the rational formula as described in the pharmacopoeias of Japan, the U.S., and Europe.

The benzalkonium chloride used in the method of the present invention may be one of those represented by the rational formula: $[CH_6H_5CH_2N(CH_3)_2R]Cl$ in which the alkyl group R is $C_8H_{17}$ to $C_{18}H_{37}$ or a mixture thereof. Preferred is a mixture mainly comprising $C_{12}H_{25}$ and $C_{14}H_{29}$, and more preferred is a mixture comprising about 80 to 85% of the compound of the rational formula in which R is $C_{12}H_{25}$ and comprising 98% or more as the total of the compound of the rational formula in which R is $C_{12}H_{25}$ and that in which R is $C_{14}H_{29}$.

The lower limit of the concentration of benzalkonium chloride added to the aqueous liquid composition in the method of the present invention is usually higher than about 0.0005%, preferably about 0.0006%, more preferably about 0.0007%, still more preferably about 0.00075%, further preferably about 0.0008%, and particularly preferably about 0.001%. The upper limit thereof is usually lower than about 0.01%, preferably about 0.005%, more preferably lower than about 0.005%, still more preferably about 0.004%, still more preferably about 0.003%, still more preferably about 0.002%, still more preferably about 0.0015%, and particularly preferably about 0.001%

The concentration range of benzalkonium chloride blended in the aqueous liquid composition in the method of the present invention is usually higher than about 0.0005% and lower than about 0.005%, preferably about 0.00075% to 0.003%, and still more preferably about 0.001% to 0.002%.

In the method of the present invention, preservatives other than benzalkonium chloride may not be used, but, an additional preservative may be used if desired. As the additional preservative, one of more kinds of, for example, chlorhexidine salt, benzethonium chloride, p-hydroxybenzonates, benzyl alcohol, p-chlorometaxylenol, chlorocresol, phenethyl alcohol, sorbic acid or a salt thereof, thimerosal, chlorobutanol, boric acid, and sodium edetate.

In the method of the present invention, the aqueous liquid composition can further contain a compound having a surface-activating action. Examples of the compound having a surface-activating action include the non-ionic surfactants and the water-soluble polymers described above. Preferably, a non-ionic surfactant is added.

The kinds of the non-ionic surfactants and the water-soluble polymers which can be blended in the method of the present invention are the same as those used in the above described aqueous liquid bromfenac composition.

These compounds having a surface-activating action may be used in combination of two or more kinds thereof. The concentrations of the added non-ionic surfactant and the added water-soluble polymer are as described above.

In the method of the present invention, the aqueous liquid composition of the present invention may contain one or more kinds of other active ingredients and/or additives appropriately selected depending on the use or the form of the composition as long as the active ingredients and/or additives do not affect the effect of the present invention. These active ingredients and/or additives may be used alone or as a mixture of two or more thereof. The blending ratio of the additional active ingredient or additive can be determined as appropriate.

Examples of the other active ingredients include an antiviral, an antimicrobial, an antifungal, an antiallergic, an antiphlogistic, a non-steroid antiphlogistic, an antibiotic, a sulfa, a synthetic penicillin, a therapeutic agent for glaucoma, a therapeutic agent for cataract, a miotic, a mydriatic, a topical astringent, a vasoconstrictor, an inhibitor for intraocular pressure increase, a therapeutic agent for ocular hypertension, a surface anesthetic, an α1-blocker, a β-blocker, a β1-blocker, a carbonate dehydratase inhibitor, a selective H1-blocker for topical use, an adrenocorticotropic hormone, vitamin B12, coenzyme type vitamin B2, an anticholinesterase drug, an organic iodine preparation, etc.

Examples of the additives include a carrier generally used for semi-solid preparations or liquid preparations (water, an aqueous solvent, an aqueous or oily base), a thickener, a saccharide, a surfactant, a preservative, a bactericide or antimicrobial, a pH adjuster, a tonicity agent, a flavor or cooling agent, a chelator, and a buffering agent.

The pH of the aqueous liquid composition containing bromfenac or a salt thereof in the method of the present invention is not particularly limited as long as the pH is acceptable to a living body and the effect of the preservative is not hindered, and is usually about 3.5 to 9, and preferably about 7 to 8.5.

The aqueous liquid composition containing bromfenac or a salt thereof in the method of the present invention may be any of a suspension, an emulsion, a gel, and an aqueous solution, but preferably an aqueous solution.

According to the method of the present invention, (b) benzalkonium chloride of which the preservative efficacy is insufficient when used alone is combined with (a) bromfenac or a salt thereof to produce an aqueous liquid composition having sufficient preservative efficacy. The aqueous liquid composition is particularly effective in reducing *Pseudomonas aeruginosa*. The presence or absence of the preservative efficacy of the aqueous liquid composition containing bromfenac or a salt thereof can be confirmed by the preservatives-effectiveness tests described above. The method of the present invention, in other words, can significantly reduce the viable cell count of *Pseudomonas aeruginosa* in an aqueous liquid composition containing bromfenac or a salt thereof. In particular, when the above-mentioned preservatives-effectiveness tests specified in the Japanese Pharmacopoeia Fifteenth Edition is conducted for the composition, the bacterial viable cell count of *Pseudomonas aeruginosa* after 14 days of storage is reduced to 0.1% of the inoculated cell count or less, and the bacterial viable cell count after 28 days of storage remains the same level as that after 14 days or less. Also, when <51> ANTIMICROBIAL EFFECTIVE- NESS TESTING (preservatives-effectiveness tests) of "Microbiological tests" specified in the United States Pharmacopeia (USP) 32 is conducted for the composition, the bacterial viable cell count after 7 days of storage is reduced to 10% of the inoculated cell count or less, the bacterial viable cell count after 14 days of storage is reduced to 0.1% of the inoculated cell count or less, and that after 28 days of storage remains the same level as that after 14 days.

Thus, the aqueous liquid composition containing bromfenac or a salt thereof, of which the concentration of benzalkonium chloride is low, causes fewer side effects and is highly safe.

The preferred use, usage, etc. of the aqueous liquid composition prepared by the method of the present invention are the same as those of the above described aqueous liquid bromfenac composition having preservative efficacy.

The present invention also provides a method for enhancing the preservative efficacy of an aqueous solution by adding bromfenac or a salt thereof to the solution. Examples of the salt of bromfenac include those used in the above-described aqueous liquid composition.

As used herein, "enhancing the preservative efficacy" means improving the action of suppressing the proliferation of at least one kind of bacteria or fungi and/or improving the action of reducing the viable cell count of at least one kind of bacteria or fungi.

According to the present invention, the preservative efficacy of an aqueous solution can be enhanced by adding bromfenac or a salt thereof to the solution, as compared to the solution without the addition. Therefore, according to the present invention, a reduced amount of a preservative is sufficient to effectively suppress the proliferation of bacteria or fungi in the aqueous solution and to effectively reduce the viable cell counts of the bacteria or fungi in the aqueous solution. The aqueous solution of which the preservative efficacy is enhanced by the method of the present invention may contain the components contained in the above-described aqueous liquid composition if desired. The method of the present invention can be advantageously used for an aqueous solution of which the preservative efficacy is insufficient and which does not comply with the requirements for the preservative efficacy specified in, for example, the Japanese Pharmacopoeia or the United States Pharmacopeia (USP). Further, the method of the present invention can be suitably used for, for example, an aqueous solution which contains a preservative but the preservative efficacy thereof is impaired under the influence of additives, such as a non-ionic surfactant or a water-soluble polymer. Examples of the aqueous solution in the method of the present invention include an aqueous solution of which the preservative efficacy is insufficient and which does not comply with the requirements for the preservative efficacy specified in, for example, the Japanese Pharmacopoeia or the United States Pharmacopeia (USP), and more preferably an aqueous solution which contains a preservative but the preservative efficacy thereof is insufficient. In particular, a preferable example is the above-described aqueous base which contains benzalkonium chloride but does not have sufficient preservative efficacy.

In the method of the present invention, examples of the bacteria include *Staphylococcus aureus*, *Escherichia coli*, and *Pseudomonas aeruginosa*; and examples of the fungi include *Candida albicans* and *Aspergillus brasiliensis* (*niger*). Inter alia, the method of the present invention is suitably used in order to enhance the effect of suppressing the proliferation of the bacteria in an aqueous solution, and/or the effect of reducing the viable cell count of the bacteria. Specifically, the enhanced effect of suppressing the proliferation of *Staphylococcus aureus* (*S. aureus*) and/or the enhanced effect of reducing the viable cell count thereof is significant. In a preferred embodiment of the present invention, the viable cell count of *S. aureus* in an aqueous solution is reduced by adding bromfenac or a salt thereof to the solution.

The method of the present invention can be suitably applied to an aqueous liquid composition, such as an ophthalmic solution, an internal solution, an injection, an external solution, an otological solution, etc., which is required to contain a reduced amount of a preservative and still to have a sufficient preservative efficacy. Inter alia, the method of the present invention is particularly useful for such an aqueous liquid composition as an ophthalmic solution in which problems such as white turbidity may arise depending on the type of the preservative.

In the method of the present invention for enhancing the preservative efficacy, the amount of bromfenac or a salt thereof to be added is preferably, for example, about 0.025% or more of the aqueous solution. The upper limit of the amount of bromfenac or a salt thereof to be added may be determined as appropriate depending on the use or the like of the aqueous solution of which the preservative efficacy is to be enhanced, but is preferably about 1%. The amount of bromfenac or a salt thereof to be added is preferably about 0.025% to 1%, and more preferably about 0.05% to 0.2%.

EXAMPLES

Hereinafter, the present invention will be illustrated in detail by Examples and Test Examples, but the invention is not limited thereto.

Test Example 1

To aqueous liquids containing 0.1% of bromfenac sodium, benzalkonium chloride was added at concentrations of 0.0005% to 0.005%, and preservatives-effectiveness tests was conducted.

1. Test Operation 1.1 Preparation of Samples of Examples 1 and 2 and Comparative Examples 1 to 7

Based on the following Table 1, the samples (aqueous liquid compositions) of Examples 1 and 2 and Comparative Examples 1 to 7 were prepared in the usual manner.

TABLE 1

| | | Examples | | Comparative Examples | | | | | | |
|---|---|---|---|---|---|---|---|---|---|---|
| | Grade | 1 | 2 | 1 | 2 | 3 | 4 | 5 | 6 | 7 |
| Bromfenac sodium hydrate | — | 0.1 g | 0.02 g | 0.1 g | — | — | — | — | — | 0.1 g |

TABLE 1-continued

|  | Grade | Examples 1 | Examples 2 | Comparative Examples 1 | Comparative Examples 2 | Comparative Examples 3 | Comparative Examples 4 | Comparative Examples 5 | Comparative Examples 6 | Comparative Examples 7 |
|---|---|---|---|---|---|---|---|---|---|---|
| Polysorbate 80 | Japanese Pharmacopoeia | 0.15 g | 0.15 g | 0.15 g | 0.15 g | 0.15 g | 0.15 g | 0.15 g | 0.15 g | 0.15 g |
| Sodium chloride | Japanese Pharmacopoeia | 0.9 g | 0.9 g | 0.9 g | 0.9 g | 0.9 g | 0.9 g | 0.9 g | 0.9 g | 0.9 g |
| Dibasic sodium phosphate hydrate | Japanese Pharmacopoeia | 0.1 g | 0.1 g | 0.1 g | 0.1 g | 0.1 g | 0.1 g | 0.1 g | 0.1 g | 0.1 g |
| Benzalkonium chloride | Japanese Pharmacopoeia | 0.001 g | 0.005 g | — | 0.001 g | 0.002 g | 0.003 g | 0.004 g | 0.005 g | 0.005 g |
| Sodium hydroxide | Special grade | q.s. | q.s. | q.s. | q.s. | q.s. | q.s. | q.s. | q.s. | q.s. |
| Purified water | — | To make 100 mL | To make 100 mL | To make 100 mL | To make 100 mL | To make 100 mL | To make 100 mL | To make 100 mL | To make 100 mL | To make 100 mL |
| pH |  | 8.3 | 8.3 | 8.3 | 8.3 | 8.3 | 8.3 | 8.3 | 8.3 | 8.3 |

In Examples 1 and 2 and Comparative Examples 1 to 7, the bromfenac sodium hydrate produced according to FDA Drug Master File #16414 were used.

The benzalkonium chloride used was a Japanese Pharmacopoeia-conforming product made by NIHON PHARMACEUTICAL CO., LTD, as a mixture of compounds of the rational formula $[C_6H_4CH_2N(CH_3)_2R]Cl$ in which R is a mixture in which the amount of $C_{12}H_{25}$ is 80 to 85% and the amount of $C_{12}H_{25}$ and $C_{14}H_{29}$ together is 98% or more.

Also used were a 10% benzalkonium chloride solution made by NIHON PHARMACEUTICAL CO., LTD, polysorbate 80 made by NOF CORPORATION, sodium chloride made by Manac Incorporated, dibasic sodium phosphate hydrate made by Wako Pure Chemical Industries, Ltd., and sodium hydroxide made by Nacalai Tesque, INC.

1.2 Operation Method

The preservatives-effectiveness tests specified in the Japanese Pharmacopoeia Fifteenth Edition was conducted. That is, each of the five strains for testing shown in Table 2 was inoculated onto the surface of a slant agar medium and precultured. As the agar medium for preculture, a soybean casein digest agar medium was used for the bacteria, and a Sabouraud glucose agar medium was used for the fungi. The bacteria were precultured at 30 to 35° C. for 18 to 24 hours, *Candida albicans* was precultured at 20 to 25° C. for 40 to 48 hours, and *Aspergillus brasiliensis* (*niger*) was precultured at 20 to 25° C. for a week or until sufficient sporulation was achieved. The samples of Examples 1 and 2 and Comparative Examples 1 to 7 were separately dispensed to 5 sterile stoppered test tubes so that each tube contained 10 mL of the sample. To these, the precultured test microorganisms shown in Table 2 below were inoculated at $10^5$ to $10^6$ cells/mL, and the thus prepared mixed samples were stored at 20 to 25° C. in light-shielded conditions. The test microorganism were not mixed with each other but separately inoculated into the samples. From each of the mixed samples, 1 mL was sampled after 1 week, 2 weeks, and 4 weeks of storage, and diluted with 9 mL of physiological saline. The same dilution was further performed twice or 3 times, and 1 mL of each diluent was transferred into separate sterile petri dishes. Subsequently, a soybean casein digest agar medium supplemented with 0.1% lecithin and 0.7% polysorbate 80 was poured into the petri dishes containing the bacteria, and a Sabouraud glucose agar medium supplemented with 0.1% lecithin and 0.7% polysorbate 80 was poured into the petri dishes containing the fungi. After culturing under the conditions shown in Table 2 below, the number of the formed colonies was counted, and the theoretical cell count in 1 mL of each mixed sample was calculated.

TABLE 2

| Strain | Medium used | Culture conditions |
|---|---|---|
| *Staphylococcus aureus* (hereinafter referred to as S.a) ATCC 6538 *Escherichia coli* (hereinafter referred to as E.c) ATCC 8739 *Pseudomonas aeruginosa* (hereinafter referred to as P.a) ATCC 9027 | Soybean casein digest agar medium supplemented with 0.1% lecithin and 0.7% polysorbate 80 | At 30 to 35° C. for about 3 to 5 days |
| *Candida albicans* (hereinafter referred to as C.a) ATCC 10231 *Aspergillus brasiliensis*(*niger*) (hereinafter referred to as A.b) ATCC 16404 | Sabouraud glucose agar medium supplemented with 0.1% lecithin and 0.7% polysorbate 80 | At 20 to 25° C. for about 5 days |

1.3 Criteria for Determination

The sample was judged as "having preservative efficacy" against a particular kind of bacteria in the cases where the sample satisfied all the following criteria: the bacterial viable cell count in the mixed solution after 14 days of storage was reduced to 0.1% of the inoculated cell count or less; and the bacterial viable cell count after 28 days of storage remained the same level as that after 14 days or less.

The sample was judged as "having preservative efficacy" against a particular kind of fungi in the cases where the fungal viable cell counts in the mixed solution after 14 days and 28 days of storage were at the same level as the inoculated cell counts or less.

In cases where the sample had preservative efficacy against all the tested strains, the sample was judged as "having preservative efficacy". In the cases where any one of the bacterial and fungal counts does not satisfy the above criteria, the sample was judged as "not having sufficient preservative efficacy".

1.4 Benzalkonium Chloride Content Measurement

1.4.1 Preparation of Sample Solution and Standard Solution

To accurately measured 2.5 mL of the sample, Diluent A (a mixture of methanol and water at a volume ratio of 7:3) was added so that the total volume was 5 mL, and thus a sample solution was prepared. Separately, to accurately measured 1 mL of the benzalkonium chloride solution (10 w/v %), Diluent A was added so that the total volume was 100 mL. To accurately measured 1 mL of the diluted benzalkonium chloride solution, Diluent A was added so that the total volume was 200 mL, and thus a standard solution was prepared. The sample solution and the standard solution each in an amount of 100 μL were subjected to liquid chromatography under the conditions shown below to determine the peak areas $A_T(C_{12})$ and $A_T(C_{14})$ of the benzalkonium chloride ($C_{12}$ and $C_{14}$) in the sample solution and the peak areas $A_S(C_{12})$ and $A_S(C_{14})$ of the benzalkonium chloride ($C_{12}$ and $C_{14}$) in the standard solution. From the determined peak areas $A_T(C_{12})$ and $A_T(C_{14})$ of the benzalkonium chloride ($C_{12}$ and $C_{14}$) in the sample solution and the peak areas $A_S(C_{12})$ and $A_S(C_{14})$ of the benzalkonium chloride ($C_{12}$ and $C_{14}$) in the standard solution, using the mathematical formula shown below, the amount of the benzalkonium chloride ($C_{12}$ and $C_{14}$) was calculated. The benzalkonium chloride ($C_{12}$) means the compound of the above rational formula in which R is $C_{12}H_{25}$. The benzalkonium chloride ($C_{14}$) means the compound of the above rational formula in which R is $C_{14}H_{29}$.

[Mathematical Formula 1]

$$\text{Amount of benzalkonium chloride } (C_{12} \text{ and } C_{14})\ (\% \text{ of labeled content}) = \frac{A_T(C_{12}) + A_T(C_{14})}{A_S(C_{12}) + A_S(C_{14})} \times 0.001/(\text{benzalkonium chloride } conc.\ (\%) \text{ as prescribed}) \times 100$$

1.4.2 HPLC Conditions for Benzalkonium Chloride Content Measurement

HPLC device (made by Shimadzu)
System controller: CBM-20A, SCL-10A$_{VP}$
Pumping unit: LC-20AD, LC-10AD$_{VP}$
Online degasser: DGU-20A$_3$, DGU-14A
UV-VIS detector: SPD-20A, SPD-10A, SPD10AV$_{VP}$
Column oven: CTO-20AC, CTO-10AC, CTO10AC$_{VP}$
Autosampler: SIL-20AC$_{NT}$, SIL-20AC, SIL-10A$_{VP}$
HPLC Operating Conditions
Detector: ultraviolet absorptiometer (measured wavelength: 214 nm)
Column: a commercially available column (made by YMC, product name YMC-Pack C8 OC12S05-1546WT, 4.6 mm×150 mm, 5 μm) which is a stainless steel tube 4.6 mm in internal diameter and 150 mm in length filled with 5-μm octylsilylated silica gel for liquid chromatography was used.
Column temperature: a constant temperature around 40° C.
Mobile phase: 15.2 g of triethylamine was dissolved in 900 mL of water, and the pH was adjusted to 2.5 with phosphoric acid. To this, 2100 mL of methanol was added and thoroughly mixed. The mixture was filtered through a membrane filter (made by Millipore, 0.45 μm HVLP, 47 mm) and then deaerated. The amount prepared was adjusted as appropriate depending on the amount needed.
Flow rate: adjusted so that the retention time of benzalkonium chloride ($C_{12}$) was about 9 minutes (1.0 mL/min).
Injector cleaner: mixture of water and methanol at 1:1 by volume
Time span of measurement: 25 minutes
Temperature of sample cooler: 20° C.

1.5 Bromfenac Content Measurement

1.5.1 Preparation of Sample Solution and Standard Solution

To accurately measured 2 mL of the sample, Diluent B (a mixture of 0.02 mol/L dibasic ammonium phosphate buffer (pH 7.3) and acetonitrile at a volume ratio of 75:25) was added so that the total volume was 20 mL, and thus a sample solution was prepared. Separately, to accurately measured 0.02 g of bromfenac sodium hydrate, Diluent B was added so that the total volume was 20 mL. To accurately measured 2 mL of the diluted bromfenac sodium hydrate solution, Diluent B was added so that the total volume was 20 mL, and thus a standard solution was prepared. The sample solution and the standard solution each in an amount of 10 μL were subjected to liquid chromatography under the conditions shown below to determine the peak area $A_T$ of bromfenac in the sample solution and the peak area $A_S$ of bromfenac in the standard solution. From the determined peak area $A_T$ of bromfenac in the sample solution and the peak area $A_S$ of bromfenac in the standard solution, using the mathematical formula shown below, the amount of bromfenac was calculated.

Amount of bromfenac sodium hydrate in sample (% of labeled content)=Amount of bromfenac in terms of anhydride in standard solution (mg)× $A_T/A_S$×5×(383.17/356.16)×0.1/(bromfenac hydrate conc. (%) as prescribed)  [Mathematical Formula 2]

1.5.2 HPLC Conditions for Bromfenac Content Measurement

HPLC device (made by Shimadzu)
System controller: CBM-20A, SCL-10A$_{VP}$
Pumping unit: LC-10AD
Online degasser: DGU-12A$_3$, DGU-20A$_3$
UV-VIS detector: SPD-10A
Column oven: CTO-10AC
Autosampler: SIL-10AC/SAMPLE COOLER
HPLC Operating Conditions
Detector: ultraviolet absorptiometer (measured wavelength: 266 nm)
Column: a commercially available column (made by SHISEIDO CO., LTD, product name CAPCELL PAKC18, SG120, 5 μm, 4.6 mm×250 mm, 5 μm) which is a stainless steel tube 4.6 mm in internal diameter and 250 mm in length filled with 5-μm octadecylsilylated silica gel for liquid chromatography was used.
Column temperature: constant temperature at around 40° C.
Mobile phase: 5.94 g of dibasic ammonium phosphate was dissolved in 2250 mL of water, and the pH was adjusted to 7.3 with phosphoric acid. To this, 750 mL of acetonitrile was added and thoroughly mixed. The mixture was filtered through a membrane filter (made by Millipore, 0.45 μm HVLP, 47 mm). The amount prepared was adjusted as appropriate depending on the amount needed.
Flow rate: adjusted so that the retention time of bromfenac was about 19 minutes (1.0 mL/min).
Injector cleaner: mixture of water and acetonitrile at 3:1 by volume Time span of measurement: 22 minutes
Temperature of sample cooler: room temperature (not controlled)

2. Results

Each sample was confirmed to contain benzalkonium chloride and bromfenac sodium hydrate as prescribed. The contents (% of labeled content) of benzalkonium chloride and bromfenac sodium hydrate in each sample are shown in Table 3.

TABLE 3

| | | Examples | | Comparative Examples | | | | | | |
|---|---|---|---|---|---|---|---|---|---|---|
| | | 1 | 2 | 1 | 2 | 3 | 4 | 5 | 6 | 7 |
| Measured content (% of prescribed value) | Bromfenac sodium hydrate | 101 | 111 | 101 | — | — | — | — | — | 102 |
| | Benzalkonium chloride | 101 | 102 | — | 101 | 101 | 99 | 99 | 98 | 100 |

The results of the preservatives-effectiveness tests are shown in Tables 4 to 11. The values in Tables 4 to 11 are the viable cell counts (cfu/mL). "*" in Table 5 to 11 means that the preservative efficacy against the tested strain was insufficient. Although the results of the viable cell counts in the preservatives-effectiveness tests are not shown for the sample of Example 2, the sample was also confirmed to have preservative efficacy as with the sample in Example 1. The decision results from the results in Tables 4 to 11 are shown in Table 12. In Table 12, "having sufficient preservative efficacy" is expressed by P (pass), and "not having sufficient preservative efficacy" is expressed by F (fail). The decision results of the preservatives-effectiveness tests are shown in Table 12. In Table 12, "having sufficient preservative efficacy" is expressed by P (pass), and "not having sufficient preservative efficacy" is expressed by F (fail).

TABLE 4

| | Example 1 (cfu/mL) | | | |
|---|---|---|---|---|
| Test microorganism | Inoculated cell count | After 7 days of storage | After 14 days of storage | After 28 days of storage |
| S.a | $3.8 \times 10^5$ | $1.0 \times 10^1$ | <10 | <10 |
| E.c | $5.4 \times 10^5$ | $2.7 \times 10^4$ | $2.0 \times 10^1$ | <10 |
| P.a | $1.4 \times 10^5$ | <10 | <10 | <10 |
| C.a | $1.4 \times 10^5$ | $9.6 \times 10^4$ | $3.5 \times 10^3$ | <10 |
| A.b | $2.4 \times 10^5$ | $2.1 \times 10^5$ | $4.1 \times 10^5$ | $2.6 \times 10^5$ |

TABLE 5

| | Comparative Example 1 (cfu/mL) | | | |
|---|---|---|---|---|
| Test microorganism | Inoculated cell count | After 7 days of storage | After 14 days of storage | After 28 days of storage |
| S.a | $3.8 \times 10^5$ | <10 | <10 | <10 |
| E.c | $5.4 \times 10^5$ | $1.4 \times 10^5$ | $1.2 \times 10^4$ * | $2.0 \times 10^2$ |
| P.a | $1.4 \times 10^5$ | $6.4 \times 10^5$ | $1.2 \times 10^6$ * | $2.1 \times 10^6$ * |
| C.a | $1.4 \times 10^5$ | $1.0 \times 10^5$ | $3.1 \times 10^4$ | <10 |
| A.b | $2.4 \times 10^5$ | $2.3 \times 10^5$ | $4.8 \times 10^5$ | $2.9 \times 10^5$ |

TABLE 6

| | Comparative Example 2 (cfu/mL) | | | |
|---|---|---|---|---|
| Test microorganism | Inoculated cell count | After 7 days of storage | After 14 days of storage | After 28 days of storage |
| S.a | $3.8 \times 10^5$ | <10 | <10 | <10 |
| E.c | $5.4 \times 10^5$ | <10 | <10 | <10 |
| P.a | $1.4 \times 10^5$ | $1.7 \times 10^3$ | $2.0 \times 10^5$ * | $4.7 \times 10^5$ * |

TABLE 6-continued

| | Comparative Example 2 (cfu/mL) | | | |
|---|---|---|---|---|
| Test microorganism | Inoculated cell count | After 7 days of storage | After 14 days of storage | After 28 days of storage |
| C.a | $1.4 \times 10^5$ | $7.7 \times 10^3$ | $3.4 \times 10^2$ | <10 |
| A.b | $2.4 \times 10^5$ | $1.8 \times 10^5$ | $3.8 \times 10^5$ | $3.8 \times 10^5$ |

TABLE 7

| | Comparative Example 3 (cfu/mL) | | | |
|---|---|---|---|---|
| Test microorganism | Inoculated cell count | After 7 days of storage | After 14 days of storage | After 28 days of storage |
| S.a | $3.8 \times 10^5$ | <10 | <10 | <10 |
| E.c | $5.4 \times 10^5$ | $1.0 \times 10^1$ | <10 | <10 |
| P.a | $1.4 \times 10^5$ | $3.3 \times 10^5$ | $3.2 \times 10^5$ * | $4.7 \times 10^5$ * |
| C.a | $1.4 \times 10^5$ | $8.6 \times 10^2$ | $1.3 \times 10^2$ | $1.0 \times 10^1$ |
| A.b | $2.4 \times 10^5$ | $1.8 \times 10^5$ | $4.3 \times 10^5$ | $5.5 \times 10^5$ * |

TABLE 8

| | Comparative Example 4 (cfu/mL) | | | |
|---|---|---|---|---|
| Test microorganism | Inoculated cell count | After 7 days of storage | After 14 days of storage | After 28 days of storage |
| S.a | $1.2 \times 10^6$ | $1.1 \times 10^4$ | <10 | <10 |
| E.c | $3.6 \times 10^6$ | $5.0 \times 10^2$ | <10 | <10 |
| P.a | $2.5 \times 10^6$ | $1.3 \times 10^6$ | $1.1 \times 10^6$ * | $1.3 \times 10^6$ * |
| C.a | $1.4 \times 10^5$ | $2.0 \times 10^1$ | $2.0 \times 10^1$ | $1.0 \times 10^1$ |
| A.b | $5.2 \times 10^5$ | $4.1 \times 10^5$ | $5.6 \times 10^5$ | $2.0 \times 10^5$ |

TABLE 9

Comparative Example 5 (cfu/mL)

| Test microorganism | Inoculated cell count | After 7 days of storage | After 14 days of storage | After 28 days of storage |
|---|---|---|---|---|
| S.a | $1.2 \times 10^6$ | <10 | <10 | <10 |
| E.c | $3.6 \times 10^6$ | $2.9 \times 10^2$ | <10 | <10 |
| P.a | $2.5 \times 10^6$ | $1.1 \times 10^6$ | $7.5 \times 10^5$ * | $2.6 \times 10^6$ * |
| C.a | $1.4 \times 10^5$ | $3.0 \times 10^1$ | <10 | <10 |
| A.b | $5.2 \times 10^5$ | $4.2 \times 10^5$ | $6.5 \times 10^5$ | $2.8 \times 10^5$ |

TABLE 10

Comparative Example 6 (cfu/mL)

| Test microorganism | Inoculated cell count | After 7 days of storage | After 14 days of storage | After 28 days of storage |
|---|---|---|---|---|
| S.a | $1.2 \times 10^6$ | <10 | <10 | <10 |
| E.c | $3.6 \times 10^6$ | $3.0 \times 10^1$ | <10 | <10 |
| P.a | $2.5 \times 10^6$ | $1.2 \times 10^6$ | $9.9 \times 10^5$ * | $9.3 \times 10^5$ * |
| C.a | $1.4 \times 10^5$ | <10 | <10 | $2.9 \times 10^2$ |
| A.b | $5.2 \times 10^5$ | $4.1 \times 10^5$ | $5.1 \times 10^4$ | $1.1 \times 10^5$ |

TABLE 11

Comparative Example 7 (cfu/mL)

| Test microorganism | Inoculated cell count | After 7 days of storage | After 14 days of storage | After 28 days of storage |
|---|---|---|---|---|
| S.a | $3.8 \times 10^5$ | <10 | <10 | <10 |
| E.c | $5.4 \times 10^5$ | $2.8 \times 10^5$ | $1.5 \times 10^5$ * | $1.7 \times 10^4$ * |
| P.a | $1.4 \times 10^5$ | $5.2 \times 10^5$ | $7.8 \times 10^5$ * | $1.6 \times 10^6$ * |
| C.a | $1.4 \times 10^5$ | $1.0 \times 10^5$ | $2.2 \times 10^4$ | $1.0 \times 10^1$ |
| A.b | $2.4 \times 10^5$ | $2.8 \times 10^5$ | $5.8 \times 10^5$ * | $2.7 \times 10^5$ |

TABLE 12

| | Ex. 1 | Ex. 2 | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|---|---|
| Preservative efficacy | P | P | F | F | F | F | F | F | F |

Ex.: Example
Com. Ex.: Comparative Example

Example 1, which contained 0.001% of benzalkonium chloride and 0.1% of bromfenac sodium, and Example 2, which contained 0.005% of benzalkonium chloride and 0.02% of bromfenac sodium, both satisfied the criteria of the preservative efficacy in the Japanese Pharmacopoeia and were determined as aqueous liquids having preservative efficacy.

However, Comparative Examples 2 to 6, prepared by adding 0.001%, 0.002%, 0.003%, 0.004%, and 0.005% of benzalkonium chloride respectively to an aqueous solution containing 0.15% of polysorbate 80 did not satisfy the criteria of the preservative efficacy in the Japanese Pharmacopoeia and were insufficient in the preservative efficacy. These results show that by combining 0.02% to 0.1% of bromfenac and 0.001% to 0.005% (insufficient for exerting preservative efficacy) of benzalkonium chloride, an aqueous liquid which satisfies the criteria of the preservative efficacy can be prepared.

In particular, the reason for the judgment of insufficient preservative efficacy in Comparative Examples 2 to 6 in Test. Example 1 was no reduction in the viable cell count of *Pseudomonas aeruginosa*. Meanwhile, Comparative Example 1 prepared by adding 0.0005% of benzalkonium chloride to an aqueous solution containing 0.15% of polysorbate 80 and 0.1% of bromfenac sodium also did not satisfy the criteria of the preservative efficacy in the Japanese Pharmacopoeia and was insufficient in the preservative efficacy. The reason for the judgment of insufficient preservative efficacy was also no reduction in the viable cell count of *Pseudomonas aeruginosa*.

Under the test conditions, while aqueous liquids containing 0.001% of benzalkonium chloride alone or 0.1% of bromfenac sodium alone did not have the effect of reducing the viable cell count of *Pseudomonas aeruginosa*, an aqueous liquid containing both 0.001% of benzalkonium chloride and 0.1% bromfenac sodium had the effect of reducing the viable cell count of *Pseudomonas aeruginosa* to a degree satisfying the criteria of the preservative efficacy in the Japanese Pharmacopoeia. The effect of reducing the viable cell count of *Pseudomonas aeruginosa* to a degree satisfying the criteria of the preservative efficacy in the Japanese Pharmacopoeia was also exerted by adding 0.02% of bromfenac sodium to 0.005% of benzalkonium chloride.

In addition, the aqueous liquid composition of Example 1 was confirmed to satisfy the criteria of the microorganism test in the U.S., that is, (1) the bacterial viable cell counts in the mixed solution after 7 days of storage is reduced to 10% of the inoculated cell count or less, the bacterial viable cell counts after 14 days of storage is reduced to 0.1% of inoculated cell count or less, and the bacterial viable cell counts after 28 days of storage is still at the same level as those after 14 days of storage or less, and (2) the fungal viable cell counts in the mixed solution after 7, 14, and 28 days of storage are all at the same level as the inoculated cell count or less.

The test results show that an aqueous liquid bromfenac composition having preservative efficacy can be prepared by adding bromfenac to an aqueous base which contains benzalkonium chloride but does not have sufficient preservative efficacy.

The test results also show that bromfenac and benzalkonium chloride synergistically enhance the preservative efficacy in an aqueous liquid.

Test Example 2

The influence of polysorbate 80, hydroxyethylcellulose, and povidone (K-30) on the preservative efficacy in a liquid containing 0.1% of bromfenac sodium and 0.001% of benzalkonium chloride was examined.

In the following Test Examples and Reference Examples, the bromfenac sodium hydrate, the benzalkonium chloride, etc. used for the preparation of samples were the same as those used in Examples 1 and 2 and Comparative Examples 1 to 7.

1. Test Operation 1.1 Preparation of Samples of Examples 3 to 7 and Comparative Examples 8 to 18

Based on the following Tables 13, 14, and 15, the samples (aqueous liquid compositions) of Examples 3 to 7 and Comparative Examples 8 to 18 were prepared in the usual manner. The povidone used was a Japanese Pharmacopoeia-conforming product made by BASF Japan.

TABLE 13

|  | Com. Ex. 8 | Com. Ex. 9 | Com. Ex. 10 | Com. Ex. 11 | Com. Ex. 12 | Com. Ex. 13 | Com. Ex. 14 |
| --- | --- | --- | --- | --- | --- | --- | --- |
| Bromfenac sodium hydrate | — | — | — | — | — | — | — |
| Polysorbate 80 | — | 0.001 g | 0.025 g | 0.04 g | 0.1 g | 0.15 g | 0.25 g |
| Sodium chloride | 0.9 g | 0.9 g | 0.9 g | 0.9 g | 0.9 g | 0.9 g | 0.9 g |
| Dibasic sodium phosphate hydrate | 0.1 g | 0.1 g | 0.1 g | 0.1 g | 0.1 g | 0.1 g | 0.1 g |
| Benzalkonium chloride | 0.001 g | 0.001 g | 0.001 g | 0.001 g | 0.001 g | 0.001 g | 0.001 g |
| Sodium hydroxide | q.s. | q.s. | q.s. | q.s. | q.s. | q.s. | q.s. |
| Purified water | To make 100 mL | To make 100 mL | To make 100 mL | To make 100 mL | To make 100 mL | To make 100 mL | To make 100 mL |
| pH | 8.3 | 8.3 | 8.3 | 8.3 | 8.3 | 8.3 | 8.3 |

Com. Ex.: Comparative Example

TABLE 14

|  | Ex. 3 | Ex. 4 | Com. Ex. 5 |
| --- | --- | --- | --- |
| Bromfenac sodium hydrate | 0.1 g | 0.1 g | 0.1 g |
| Polysorbate 80 | 0.001 g | 0.15 g | 0.25 g |
| Sodium chloride | 0.9 g | 0.9 g | 0.9 g |
| Dibasic sodium phosphate hydrate | 0.1 g | 0.1 g | 0.1 g |
| Benzalkonium chloride | 0.001 g | 0.001 g | 0.001 g |
| Sodium hydroxide | q.s. | q.s. | q.s. |
| Purified water | To make 100 mL | To make 100 mL | To make 100 mL |
| pH | 8.3 | 8.3 | 8.3 |

Ex.: Example
Com. Ex.: Comparative Example

TABLE 15

|  | Com. Ex. 16 | Ex. 5 | Ex. 6 | Com. Ex. 17 | Com. Ex. 18 | Ex. 7 |
| --- | --- | --- | --- | --- | --- | --- |
| Bromfenac sodium hydrate | — | 0.1 g | 0.1 g | 0.1 g | — | 0.1 g |
| Hydroxyethyl cellulose | 0.05 g | 0.05 g | 0.3 g | 0.5 g | — | — |
| Povidone (K30) | — | — | — | — | 1.4 g | 1.4 g |
| Polysorbate 80 | — | — | — | — | — | — |
| Sodium chloride | 0.9 g | 0.9 g | 0.9 g | 0.9 g | 0.9 g | 0.9 g |
| Dibasic sodium phosphate hydrate | 0.1 g | 0.1 g | 0.1 g | 0.1 g | 0.1 g | 0.1 g |
| Benzalkonium chloride | 0.001 g | 0.001 g | 0.001 g | 0.001 g | 0.001 g | 0.001 g |
| Sodium hydroxide | q.s. | q.s. | q.s. | q.s. | q.s. | q.s. |
| Purified water | To make 100 mL | To make 100 mL | To make 100 mL | To make 100 mL | To make 100 mL | To make 100 mL |
| pH | 8.3 | 8.3 | 8.3 | 8.3 | 7.4 | 7.5 |

Ex.: Example
Com. Ex.: Comparative Example

1.2 Operation Method

The aqueous liquid compositions of Examples 3 to 7 and Comparative Examples 8 to 15 were subjected to the preservatives-effectiveness tests according to 1.2 Operation Method and 1.3 Criteria for Determination of the above Test Example 1

2. Results

The results of the preservatives-effectiveness tests are shown in Tables 16 and 17. In Tables 16 and 17, "having sufficient preservative efficacy" is expressed by P (pass), and "not having sufficient preservative efficacy" is expressed by F (fail).

TABLE 16

| | Com. Ex. 8 | Com. Ex. 9 | Com. Ex. 10 | Com. Ex. 11 | Com. Ex. 12 | Com. Ex. 13 | Com. Ex. 14 | Ex. 3 | Ex. 4 | Com. Ex. 15 |
|---|---|---|---|---|---|---|---|---|---|---|
| Preservative efficacy | P | P | F | F | F | F | F | P | P | F |

Ex.: Example
Com. Ex.: Comparative Example

TABLE 17

| | Com. Ex. 16 | Ex. 5 | Ex. 6 | Com. Ex. 17 | Com. Ex. 18 | Ex. 7 |
|---|---|---|---|---|---|---|
| Preservative efficacy | F | P | P | F | F | P |

Ex.: Example
Com. Ex.: Comparative Example

While the bases containing 0.001% of benzalkonium chloride passed the preservatives-effectiveness tests (for example, Comparative Example 8), in the cases where 0.025% or more of polysorbate 80 existed in the solution containing 0.001% of benzalkonium chloride, the solution did not satisfy the criteria of the preservative efficacy (Comparative Examples 10 to 14). However, even in the cases where 0.025% to lower than 0.25% of polysorbate 80 was contained, when 0.1% of bromfenac was added, the liquid satisfied the criteria of the preservative efficacy in the Japanese Pharmacopoeia (Example 4). The results show that even when the preservative efficacy was impaired due to the addition of polysorbate 80 to the base, a combination of bromfenac and benzalkonium chloride enhanced the preservative efficacy.

While the bases containing 0.001% of benzalkonium chloride passed the preservatives-effectiveness tests (for example, Comparative Example 8), in the case where 0.05% or more of hydroxyethylcellulose existed in the solution containing 0.001% of benzalkonium chloride, the solution did not satisfy the criteria of the preservative efficacy (Comparative Example 16). However, even in the cases where 0.05% to lower than 0.5% of hydroxyethylcellulose was contained, when 0.1% of bromfenac was added, the liquid satisfied the criteria of the preservative efficacy in the Japanese Pharmacopoeia (Examples 5 and 6). The results show that even when the preservative efficacy was impaired due to the addition of hydroxyethylcellulose to the base, a combination of bromfenac and benzalkonium chloride enhanced the preservative efficacy. It was also shown that even when a base to which povidone (K-30) had been added was used (Comparative Example 18), a combination of bromfenac and benzalkonium chloride enhanced the preservative efficacy (Example 7).

Test Example 3

The preservative efficacy of bromfenac liquids containing 0.001% of benzalkonium chloride together with a non-ionic surfactant other than polysorbate 80 was examined.

1. Test Operation

1.1 Preparation of Samples of Examples 8 and 9

Based on the following Table 18, the samples (aqueous liquid compositions) of Examples 8 and 9 and Comparative Example 19 were prepared in the usual manner. The polyoxyethylene hydrogenated castor oil 60 used was made by Wako Pure Chemical and the polyoxyl 40 stearate used was a Japanese Pharmacopoeia-conforming product made by Nihon Surfactant Kogyo.

TABLE 18

| | Ex. 8 | Ex. 9 | Com. Ex. 19 |
|---|---|---|---|
| Bromfenac sodium hydrate | 0.1 g | 0.1 g | — |
| Polyoxyethylene hydrogenated castor oil 60 | 0.15 g | — | — |
| Polyoxyl 40 stearate | — | 0.05 g | 0.05 g |
| Sodium chloride | 0.9 g | 0.9 g | 0.9 g |
| Dibasic sodium phosphate hydrate | 0.1 g | 0.1 g | 0.1 g |
| Benzalkonium chloride | 0.001 g | 0.001 g | 0.001 g |
| Sodium hydroxide | q.s. | q.s. | q.s. |
| Purified water | To make 100 mL | To make 100 mL | To make 100 mL |
| pH | 8.3 | 8.3 | 8.3 |

Ex.: Example
Com. Ex.: Comparative Example

1.2 Operation Method

The aqueous liquid compositions of Examples 8 and 9 and Comparative Example 19 were subjected to the preservatives-effectiveness tests according to 1.2 Operation Method and 1.3 Criteria for Determination of the above Test Example 1.

2. Results

The results of the preservatives-effectiveness tests are shown in Table 19. In Table 19, "having sufficient preservative efficacy" is expressed by P (pass), and "not having sufficient preservative efficacy" is expressed by F (fail).

TABLE 19

|  | Ex. 8 | Ex. 9 | Com. Ex. 19 |
|---|---|---|---|
| Preservative efficacy | P | P | F |

Ex.: Example
Com. Ex.: Comparative Example

Table 19 shows that, as with the case where polysorbate 80 is used, a bromfenac liquid composition containing 0.001% of benzalkonium chloride and satisfying the criteria of the preservative efficacy can be prepared even with the use of polyoxyethylene hydrogenated castor oil 60 and polyoxyl 40 stearate as a non-ionic surfactant.

Test Example 4

1. Test Operation 1.1 Preparation of Samples of Examples 10 to 13

A liquid concentrate containing 2% (w/v) of bromfenac sodium was prepared by dissolving 4 g of bromfenac sodium in physiological saline so that the total volume was 200 mL, followed by sterilization using a 0.22-μm filter. The liquid concentrate was diluted with Muller-Hinton Broth (MHB medium, made by Difco) to prepare liquid media each containing 0.0125%, 0.025%, 0.05%, or 0.2% of bromfenac sodium, which were used as samples of Examples 10, 11, 12, and 13, respectively. These samples were all clear and at pH 7.2, and had osmotic pressure of 280 mOsm (Example 10), 281 mOsm (Example 11), 284 mOsm (Example 12), and 290 mOsm (Example 13).

1.2 Operation Method

In each well of a 96 well plate having round bottom wells (made by Corning), 100 μL of each sample and 5 μL of *Staphylococcus aureus* bacterial liquid were placed (n=3), and mixed by pipetting to prepare mixed solutions of each sample. Each mixed solution contained about $8.7 \times 10^4$ cfu/well of *Staphylococcus aureus*. The mixed solutions were cultured at about 35° C. for 18 to 24 hours, and then bacterial proliferation in each well was observed. Evaluation was performed based on the presence or absence of bacterial precipitates and the size of the precipitates.

2. Results

After the culture, bacterial precipitates of more than 1 mm in diameter were observed in the sample of Example 10 containing 0.0125% of bromfenac sodium, and bacterial precipitates of 1 mm or less in diameter were observed in the sample of Example 11 containing 0.025% of bromfenac sodium. No bacterial precipitates were observed in the sample of Example 12 containing 0.05% of bromfenac sodium and the sample of Example 1.3 containing 0.2% of bromfenac sodium. These results show that, with the increase in the amount of added bromfenac sodium, the diameter of bacterial precipitates decreases, and at further higher concentrations of bromfenac sodium, no bacterial precipitates are observed. The above results show that bromfenac can enhance the preservative efficacy of an aqueous solution and reduce the viable cell count of, in particular, *Staphylococcus aureus*.

Reference Examples 1 and 2

1. Test Operation 1.1 Preparation of Samples of Reference Examples 1 and 2

Based on the following Table 20, the samples (aqueous liquid compositions) of Reference Examples 1 and 2 were prepared in the usual manner. The hydroxyethylcellulose used was the one made by Wako Pure Chemical.

TABLE 20

|  | Reference Example 1 | Reference Example 2 |
|---|---|---|
| Bromfenac sodium hydrate | 0.1 g | 0.1 g |
| Hydroxyethyl cellulose | 5 g | 5 g |
| Polysorbate 80 | 2 g | 2 g |
| Boric acid | 0.025 g | 0.025 g |
| Borax | 0.025 g | 0.025 g |
| Benzalkonium chloride | 0.001 g | 0.001 g |
| Anhydrous sodium sulfite | 2 g | — |
| Sodium hydroxide | q.s. | q.s. |
| Purified water | To make 100 mL | To make 100 mL |
| pH | 8.3 | 8.3 |

1.2 Operation Method

The aqueous liquid compositions of Reference Examples 1 and 2 were subjected to the preservatives-effectiveness tests according to 1.2 Operation Method and 1.3 Criteria for Determination of the above Test Example 1.

2. Results

The results of the preservatives-effectiveness tests are shown in Table 21. In Table 21, "having sufficient preservative efficacy" is expressed by P (pass), and "not having sufficient preservative efficacy" is expressed by F (fail).

TABLE 21

|  | Reference Example 1 | Reference Example 2 |
|---|---|---|
| Preservative efficacy | P | F |

Table 21 shows that while the aqueous liquid composition of Reference Examples 1, which contained 0.1% of bromfenac, 5% of hydroxyethylcellulose, 2% of polysorbate 80, and 2% of sodium sulfite, satisfied the criteria of the preservative efficacy in the Japanese Pharmacopoeia, the aqueous liquid composition of Reference Examples 2, which contained 0.1% of bromfenac, 5% of hydroxyethylcellulose, and 2% of polysorbate 80, did not. It was revealed that the preservative efficacy of the aqueous liquid composition of Reference Examples 1 is based on the effect of the 2% of sodium sulfite.

3. Conclusion

The inventors confirmed that even in the cases where an aqueous base contained 0.001% to 0.005% of benzalkonium chloride, when the aqueous base further contained more than a certain amount of polysorbate 80, hydroxyethylcellulose, or povidone, the preservative efficacy was insufficient. The reason for the judgment of insufficient preservative efficacy of the aqueous base was the test results for *Pseudomonas aeruginosa*.

Meanwhile, it was also confirmed that the preservative efficacy of the bromfenac/polysorbate 80 aqueous liquid composition, which contained 0.1% of bromfenac, was also insufficient. The reason for the judgment of insufficient preservative efficacy of the aqueous liquid composition was also the test results for *Pseudomonas aeruginosa*, the same bacterium as in the above case of the benzalkonium chloride/polysorbate 80 aqueous base.

Thus, the inventors prepared aqueous bases containing 0.001% of benzalkonium chloride together with more than a certain amount of a surfactant or a water-soluble polymer such as polysorbate 80, hydroxyethylcellulose, and povidone, and found that, although the preservative efficacy of each of them was insufficient, an aqueous liquid composition containing bromfenac, benzalkonium chloride, and a surfactant or a water-soluble polymer has preservative efficacy.

The inventors also confirmed that the aqueous liquid composition containing bromfenac, benzalkonium chloride, and a surfactant or a water-soluble polymer had the preservative efficacy complying with <51> ANTIMICROBIAL EFFECTIVENESS TESTING (preservatives-effectiveness tests) of "Microbiological tests" specified in the United States Pharmacopeia (USP) 32.

It is also known that a combination of a non-steroidal anti-inflammatory drug (NSAID) and a quaternary ammonium salt, such as benzalkonium chloride, forms a complex, resulting in decline in the preservative efficacy. Since bromfenac is non-steroidal and benzalkonium chloride is a quaternary ammonium salt, it is expected that a combination of these two results in decline in the preservative efficacy. However, unexpectedly, a combination of bromfenac and benzalkonium chloride, both of which were at a concentration insufficient for exerting preservative efficacy by itself, produced an aqueous liquid composition having preservative efficacy.

INDUSTRIAL APPLICABILITY

According to the present invention, an aqueous liquid bromfenac composition which causes fewer side effects and is safe and stable can be provided. Therefore, the aqueous liquid preparation of the present invention is useful in the pharmaceutical field, and suitably used as, for example, an ophthalmic solution, a nasal solution, or an otic solution.

The invention claimed is:

1. A method for enhancing the preservative efficacy of an aqueous solution, the method comprising adding bromfenac or a salt thereof to the aqueous solution,
   wherein the amount of bromfenac or a salt thereof added to the aqueous solution is 0.05% to 0.15%,
   wherein the aqueous solution is an aqueous base which contains (a) 0.001 to 0.002% of benzalkonium chloride and (b) 0.025% or higher and lower than 0.25% of a non-ionic surfactant,
   and wherein the aqueous solution has preservative efficacy with said bromfenac or salt thereof but does not have sufficient preservative efficacy without said bromfenac or salt thereof.

2. The method of claim 1, wherein the enhancement of the preservative efficacy is evidenced by reduction in viable cell count of *Pseudomonas aeruginosa*.

3. The method of claim 1, wherein the non-ionic surfactant is polysorbate 80.

* * * * *